(12) United States Patent
Duan et al.

(10) Patent No.: US 7,128,850 B2
(45) Date of Patent: Oct. 31, 2006

(54) ELECTRICALLY CONDUCTIVE SI-TI-C-N CERAMICS

(75) Inventors: Ren-Guan Duan, Davis, CA (US);
Joshua D. Kuntz, Lafayette, CA (US);
Amiya K. Mukherjee, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 151 days.

(21) Appl. No.: 10/453,879

(22) Filed: Jun. 2, 2003

(65) Prior Publication Data

US 2004/0238795 A1    Dec. 2, 2004

(51) Int. Cl.
*C04B 35/596* (2006.01)
*C04B 35/56* (2006.01)
*C04B 35/58* (2006.01)
*H01B 1/06* (2006.01)
*B28B 3/00* (2006.01)

(52) U.S. Cl. ............... 252/518.1; 252/519.1; 252/500; 501/97.4; 501/87; 501/91; 501/92; 264/625; 264/626; 264/682; 264/683

(58) Field of Classification Search ............... 252/500, 252/502, 518.1, 519.1; 501/87, 91–93, 97.4; 219/553; 264/125, 332, 430, 625, 682, 683
See application file for complete search history.

(56) References Cited

U.S. PATENT DOCUMENTS

| | | | |
|---|---|---|---|
| 4,929,704 A | 5/1990 | Schwark | |
| 5,001,090 A | 3/1991 | Schwark | |
| 5,021,533 A | 6/1991 | Schwark | |
| 5,032,649 A | 7/1991 | Schwark | |
| 5,041,515 A * | 8/1991 | Takeda et al. | 528/34 |
| 5,066,423 A * | 11/1991 | Kubo et al. | 252/516 |
| 5,081,078 A * | 1/1992 | Peuckert et al. | 501/96.3 |
| 5,155,181 A | 10/1992 | Schwark | |
| 5,322,825 A * | 6/1994 | Leung et al. | 501/92 |
| 5,356,842 A * | 10/1994 | Yamakawa et al. | 501/87 |
| 5,498,855 A * | 3/1996 | Deevi et al. | 219/553 |
| 6,458,315 B1* | 10/2002 | Seitz et al. | 264/625 |
| 6,544,657 B1* | 4/2003 | Motz et al. | 428/446 |

FOREIGN PATENT DOCUMENTS

DE    WO 99/41211    * 11/2000

OTHER PUBLICATIONS

Gasch et al, "Preparation of a Si3N4/SiC nanocomposite by high-pressure sintering of polymer precursor derived powders," *Scripta Materialia*, 2001, 45, 1063-1068).*

Herrmann et al, "Densification, Microstructure and Properties of Si3N4-Ti(C,N) Composites," J. Eur. Cer. Soc., 1993, 12, 287-296.*

Motz et al, "Novel ceramic-like Coatings from organomeetallic Precursors," British Ceramic Proceedings (UK)-1999.*

Haluschka et al, "Silicon carbonitride ceramics derived from polysilazaners Part II. Investigation of electrical properties," J. Eur. Cer. Soc., 2000, 20, 1365-1374.*

Kion International, "Kion™ Inorganic Polymers Coatings / Engineering Plastics / Ceramics", http://www.kioncorp.com/.

Patscheider et al., "Plasma-Induced Deposition of Titanium Nitride from $TiCl_4$ in a Direct Current Glow Discharge: Control of the Chlorine Content and Gas-Phase Nucleation", *Plasma Chemistry and Plasma Processing* 16:3: 341-363 (1996).

Hermann et al., "Sinterverhalten, Gefuge und Eigenschaften von $TIC_xN_{(1-x)}/Si_3N_4$-Verbundwerkstoffen", *DKG* 73: 434-445 (1996).

Riedel et al., "Synthesis of dense silicon-based ceramics at low temperatures", *Nature* 355: 714-717 (1992).

Riedel et al., "A covalent micro/nano-composite resistant to high-temperature oxidation", *Nature* 374: 526-528 (1995).

Bill et al., "Precursor-Derived Covalent Ceramics", *Adv. Mater.* 7:9: 775-782 (1995).

Wan et al., "Silicon carbonitride ceramics produced by pyrolysis of polymer ceramic precursor", *J. Mater. Res.* 15:8:1657-1660 (2000).

Wan et al., "Effect of Ammonia Treatment on the Crystallization of Amorphous Silicon-Carbon-Nitrogen Ceramics Derived from Polymer Precursor Pyrolysis", *J. Am. Ceram. Soc.* 85:3: 554-584 (2002).

Herrmann et al., "Densification, Microstructure and Properties of $Si_3N_4$-Ti(C,N) Composites", *Journal of the European Ceramic Society* 12: 287-296 (1993).

Duan et al., "Stability of intergranular phases in hot-pressed $Si_3N_4$ studied with mechanical spectroscopy and in-situ high-temperature XRD", *Journal of the European Ceramic Society* 22: 1897-1904 (2002).

(Continued)

*Primary Examiner*—Douglas McGinty
*Assistant Examiner*—Kallambella Vijayakumar
(74) *Attorney, Agent, or Firm*—M. Henry Heines; Townsend and Townsend and Crew, LLP

(57) ABSTRACT

Composite materials containing silicon, titanium, carbon, and nitrogen, formed by spark plasma sintering of ceramic starting materials to a high relative density, demonstrate unusually high electrical conductivity as well as high-performance mechanical and chemical properties including hardness, fracture toughness, and corrosion resistance. This combination of electrical, mechanical, and chemical properties makes these composites useful as electrical conductors in applications where high-performance materials are needed due to exposure to extreme conditions such as high temperatures, mechanical stresses, and corrosive environments.

22 Claims, No Drawings

OTHER PUBLICATIONS

Duan et al., "Thermal stability of in situ formed $Si_3N_4$-$Si_2N_2O$-TiN composites", *Journal of the European Ceramic Society* 22: 2527-2535 (2002).

Boskovic et al., "Liquid-Phase Sintering and Properties of $Si_3N_4$-TiN Composites", *Journal of Materials Synthesis and Processing* 7:2: 119-126 (1999).

An et al., "Newtonian Viscosity of Amorphous Silicon Carbonitride at High Temperature", *J. Am. Ceran. Soc.* 81:5: 1349-1352 (1998).

Ziegler et al., "Synthesis, microstructure and properties of SiCN ceramics prepared from tailored polymers", *Materials Chemistry and Physics* 61: 55-63 (1999).

Liew et al., "Processing and characterization of silicon carbonnitride ceramics: application of electrical properties towards MEMS thermal actuators", *Sensors and Actuators* 103: 171-181 (2003).

Gasch et al., "Preparation of a $Si_3N_4$/SiC nanocomposite by highpressure sintering of polymer precursor derived powders", *Scripta Materialia* 45: 1063-1068 (2001).

Haluschka et al., "Silicon carbonitride ceramics derived from polysilazanes Part II. Investigation of electrical properties", *Journal of the European Ceramic Society* 20: 1365-1374 (2000).

Hermann et al., "Structure and Electronic Transport Properties of Si-(B)-C-N Ceramics", *J. Am. Ceram. Soc.* 84: 2260-2264 (2001).

Ramakrishnan et al., "Silicoboron-carbonitride ceramics: A class of high-temperature, dopable electronic materials", *Applied Physics Letters* 78:20: 3076-3078 (2001).

Shah et al., "Mechanical properties of a fully dense polymer derived ceramic made by a novel pressure casting process", *Acta Materialia* 50: 4093-4103 (2002).

Veprek et al., "Recent progress in the superhard nanocrystalline composites: towards their industrialization and understanding of the origin of the superhardness", *Surface and Coatings Technology* 108-109: 138-147 (1998).

Accuratus, "Silicon Nitride $Si_3N_4$", http://www.accuratus.com/silinit.html.

Cercom, Inc., "Sintered and Reaction Bonded Silicon Nitride", http://www.10.thomasregister.com/olc/cercom/sn.htm.

Cercom, Inc., ""PAD" Silicon Carbide", http://www.10.thomasregister.com/olc/cercom/scb.htm.

* cited by examiner

ELECTRICALLY CONDUCTIVE SI-TI-C-N CERAMICS

STATEMENT AS TO RIGHTS TO INVENTIONS MADE UNDER FEDERALLY SPONSORED RESEARCH OR DEVELOPMENT

This invention was made with Government support under Contract No. N00014-03-1-0148, awarded by the United States Office of Naval Research. The Government has certain rights in this invention.

BACKGROUND OF THE INVENTION

1. Field of the Invention

This invention resides in the field of electrically conductive ceramics, and incorporates technologies relating to nanocrystalline materials and sintering methods for densification and property enhancement of materials.

2. Description of the Prior Art

The ability of ceramics to withstand extreme conditions of temperature, mechanical stress, and chemical exposure without failure or with at most a very low failure rate has led to the use of ceramics in high-performance applications, such as heat engines, cutting tools, wear and friction surfaces, and space vehicles. In recent years, the use of ceramics has extended into the fields of microtechnology and nanotechnology, since the high-performance characteristics of ceramics has made them attractive candidates for meeting the increasing demands of nano-scale electronics and microelectromechanical systems (MEMS).

In addition to their mechanical properties, certain ceramics are of increasing interest for their ability to conduct electricity since various kinds of electrical devices are being designed for use in environments that require temperature resistance, high strength, and chemical inertness. In the microelectronics industry, for example, ceramics are used as substitutes for silicon, as trays and wafer carriers, and as ruggedized microchip substrates. In microwave technologies, conductive ceramics are attractive for their ability to perform effectively in high-temperature environments while absorbing or shielding components from electromagnetic interference. In the automotive industry, the high-temperature, high-strength, chemically inert, and electrically conductive character of ceramics make them attractive candidates for components such as fuel injector assemblies. The need for these qualities extends to medicine as well, since a variety of medical devices, such as implants, prostheses, and surgical devices, would benefit from a combination of electrical functionality, high strength and chemical inertness. This combination of properties is also of benefit to electrodes used in electrical power supplies such as batteries and solid oxide fuel cells. A similar need exists in analytical and testing devices for materials used as chemical sensors, gas separation materials, and materials for hydrogen absorption. In the aerospace and defense industries as well, materials with these properties are needed for aircraft and aircraft engines and for thermal management materials in human spaceflight applications.

Although ceramics are traditionally known as electrical insulators, ceramics can be made conductive in various ways. In amorphous SiCN-based ceramics, one way is by adding dopants to form electrically conductive composites. This method has been investigated by Hermann, A. M., et al., *J. Am. Ceram. Soc.* 84, 2260–2264 (2001), and Ramakrishnan, P. A., et al., *Applied Phys. Lett.* 78, 3076–3078 (2001), who used boron as a dopant for Si—C—N ceramics and reported that the resulting Si—B—C—N has a conductivity of about 10 $(\Omega \cdot m)^{-1}$. Another method is by annealing the ceramic above its pyrolysis temperature. Amorphous silicon-carbon-nitride ceramics that are derived from polymers can be made conductive in this manner. Haluschka, C., et al., *J. Eur. Ceram. Soc.* 20, 1365–1374 (2000) report that the electrical conductivity of amorphous Si—C—N ceramics at room temperature can range from $10^{-13}$ to $10^2$ $(\Omega \cdot m)^{-1}$ depending on the pyrolysis atmosphere and subsequent heat treatments, and that the electrical conductivity has a positive temperature coefficient. In general, however, the published literature on Si—C—N and Si—B—C—N indicates that the electrical conductivity of these ceramics is only moderate.

A further disadvantage of Si—C—N and Si—B—C—N ceramics is reported by Shah, S. R., et al., *Acta Materialia* 50, 4093–4103 (2002), who state that the polymerization of the polymeric precursor to form the amorphous material is often accompanied by the evolution of ammonia which introduces pores into the material and also hinders the crosslinking process. Ceramic samples prepared in this manner typically have a porosity of about 10%, with a pore size of the same order or magnitude as the particle size of the powder. This results in poor mechanical properties which, together with an electrical conductivity that is only moderate, limits the use of Si—C—N and Si—B—C—N ceramics in both structural and functional applications.

While amorphous Si—C—N ceramics typically have poor mechanical properties, these properties can be improved by crystallization of the amorphous Si—C—N at high-temperature to form $Si_3N_4/SiC$ composites. See Bill, J., et al., *Advanced Materials* 7, 775–787 (1995). Unfortunately, the electrical conductivity of the crystallized product is relatively low due to the combination of the SiC which is semi-conducting and the $Si_3N_4$ which is electrically insulating. Entirely separate from $Si_3N_4/SiC$ composites and Si—C—N ceramics in general are titanium carbide, titanium carbonitride, and titanium nitride, which exhibit both high electrical conductivity and excellent mechanical properties but are difficult to sinter to full density. TiCN and TiN are primarily used as thin layers that are formed by chemical or physical deposition, as reported by Patscheider, J., et al., *Plasma Chemistry and Plasma Processing* 16, 341–363 (1996), and Veprek, S., et al., *Surf. Coat. Technol.* 109, 138–147 (1998). $TiC_xN_{1-x}$ is also used as an additive to $Si_3N_4$ ceramics for purposes of increasing strength and improving electrical conductivity, as reported by Duan, R.-G., *J. Eur. Ceram. Soc.* 22, 2527–2535 (2002); Duan, R.-G., *J Eur. Ceram. Soc.* 22, 1897–1904 (2002); Herrmann, M., et al., *CFI-Ceramic Forum International* 73, 434–445 (1996); Bogkovic, S., et al., *J. Mater. Synthesis and Processing* 7, 119–126 (1999); and Herrmann, M., et al., *J Eur. Ceram. Soc.* 12, 287–296 (1993). The procedures reported in these papers involved sintering of the materials into composites by hot pressing, and the papers demonstrate that the addition of the TiN resulted in an increase in electrical conductivity from $10^{-10}$ $(\Omega \cdot m)^{-1}$ for sintered $Si_3N_4$ to $10^3$ $(\Omega \cdot m)^{-1}$ for a sintered $Si_3N_4/TiN$ composite containing 30 vol % TiN. Thus, while the TiN improved the electrical conductivity, the resulting value was still relatively low.

Of further relevance to this invention is the literature on electric field-assisted sintering, which is also known as spark plasma sintering, plasma-activated sintering, and field-assisted sintering technique. This process is disclosed in the literature for use on metals and ceramics, for consolidating polymers, for joining metals, for crystal growth, and for promoting chemical reactions. The densification of alumina powder by spark plasma sintering is disclosed by Wang, S. W., et al., *J. Mater. Res.* 15(4)(April 2000): 982–987.

All citations appearing in this specification, including published papers, patents and Internet websites, are hereby incorporated herein by reference in their entirety for all purposes legally capable of being served thereby.

SUMMARY OF THE INVENTION

It has now been discovered that a composite material formed by spark plasma sintering of a powder mixture of titanium dioxide and a silicon carbon nitrogen material exhibits an electrical conductivity that is comparable to that of electrically conductive metals, while also exhibiting favorable mechanical properties, notably high hardness and fracture toughness, as well as a low theoretical density. The silicon carbon nitrogen component of the powder mixture used as a starting material is either an amorphous silicon carbonitride powder or a powder of a crystalline $Si_3N_4/SiC$ combination. The titanium dioxide is preferably in crystalline form, and when this is combined with an amorphous silicon carbonitride powder, the invention entails the unique sintering of a combination of crystalline and amorphous materials and the discovery that this can produce a microstructure with these highly favorable electrical and mechanical characteristics.

In preferred embodiments of this invention, the powder mixture consists of nano-sized particles, and sintering is performed to achieve theoretical densities that approach 100%. This further enhances the properties of the final product. These and other features, advantages and objects of this invention will be apparent from the description that follows.

DETAILED DESCRIPTION OF THE INVENTION AND PREFERRED EMBODIMENTS

The silicon carbon nitrogen component of the powder mixture used in the practice of this invention can be obtained by the pyrolysis of polymeric precursors that contain silicon, carbon, and nitrogen, or by a mixture or combination of crystalline $Si_3N_4$ and silicon carbide. When the first of these alternatives is used, examples of suitable polymeric precursors are polyorganosilazanes, as disclosed in the following United States patents:

Schwark (Hercules Incorporated, assignee), U.S. Pat. No. 4,929,704, issued May 29, 1990

Schwark (Hercules Incorporated, assignee), U.S. Pat. No. 5,001,090, issued Mar. 19, 1991

Schwark (Hercules Incorporated, assignee), U.S. Pat. No. 5,021,533, issued Jun. 4, 1991

Schwark (Hercules Incorporated, assignee), U.S. Pat. No. 5,032,649, issued Jul. 16, 1991

Schwark (Hercules Incorporated, assignee), U.S. Pat. No. 5,155,181, issued Oct. 13, 1992

Further descriptions of polyorganosilazanes are found in the following publications available on the Internet at www.kioncorp.com:

"KiON™ Polysilazanes—Hybrid Inorganic/Organic Resin Systems," KiON Corporation, New York, N.Y., USA, Apr. 2, 2001

"KiON™ VL20 and CERASET™ Liquid Polysilazanes—General Technical Bulletin," KiON™Corporation, New York, N.Y., USA, Apr. 2, 2001

These polymers are liquid and are generally characterized by repeat units with alternating silicon and nitrogen atoms. Some of these polymers further contain urea or thiourea functionalities in the repeat units, and in some cases the repeat units are cyclic while others have acyclic repeat units. One preferred polyorganosilazane is CERASET™ SN, whose formula is shown below:

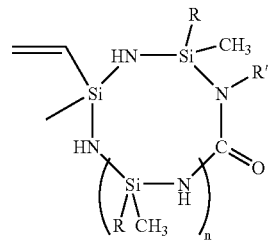

in which R and R' independently represent either a hydrogen atom or a vinyl group and n ranges from 1 to 20. Another preferred polyorganosilazane is KiON™ VL20 whose structure is similar to that of CERASET™ SN but lacks the urea functionalities. These polymers are available from commercial suppliers such as Commodore Polymer Technologies (Columbus, Ohio, USA).

Prior to pyrolysis, the polyorganosilazanes are preferably crosslinked, which can be achieved by exposure to heat in an inert atmosphere such as nitrogen or argon, such as for example at a temperature of 200–400° C. for a short period of time such as 15 minutes to 40 minutes. Further crosslinking, if desired, can be achieved by heating to higher temperature in the presence of a free radical generator such as a peroxide. Pyrolysis can be performed on the crosslinked material by heating to a temperature of 1,300° C. to 1,500° C. for a longer period of time such as 0.5 hour to 6 hours, again in an inert atmosphere. These treatments convert the liquid precursor to a solid ceramic material.

In embodiments of the invention in which crystalline silicon nitride and silicon carbide are used in place of an amorphous pyrolysis product of a polyorganosilazane, the crystalline silicon nitride and silicon carbide can be purchased from ceramics suppliers. Silicon nitride is available, for example, from Nanostructured and Amorphous Materials, Inc. (Los Alamos, N. Mex., USA), Ceradyne Inc. (Costa Mesa, Calif., USA), and Cercom Inc. (Vista, Calif., USA). Silicon carbide is available from Cercom Inc. and other suppliers to the ceramics industry.

Titanium dioxide is likewise available from ceramics suppliers such as, for example, Nanophase Technologies Corporation (Burr Ridge, Ill., USA).

The relative amounts of silicon, carbon, and nitrogen in the Si—C—N component of the powder mixture can vary, although some variation in electrical and mechanical properties may result as the proportion of any one element is raised or lowered. For the purposes of this invention, best results will be obtained when the relative amounts are about 10 to about 60 parts by volume silicon, about 10 to about 60 parts by volume carbon, and about 10 to about 60 parts by volume nitrogen, based on a total of 100 parts by volume of the Si—C—N component. Preferred ranges are about 10 to about 30 parts by volume silicon, from about 25 to about 50 parts by volume carbon, and from about 25 to about 50 parts by volume nitrogen, based on a total of 100 parts by volume of said component. The volumes used in determining these parts by volume are calculated from the weight percents of the bulk starting materials and the theoretical density of each component. The proportion of titanium dioxide to the Si—C—N component can also vary, and here as well, some variation in electrical and mechanical properties may occur as a result. In general, best results will be obtained with powder mixtures in which the titanium dioxide constitutes from about 10% to about 40% by weight of the mixture.

The starting titanium dioxide material is preferably in the form of a nano-sized powder, while the starting SiCN component is preferably in the form of a micro-sized powder. The prefix "nano" as used herein generally refers to dimensions that are less than 100 nm. Preferred average particle sizes for the Si—C—N component are within the range of from about 1 to about 20 microns, and preferred average particle sizes for the titanium dioxide are within the range of about 10 to about 50 nm. In addition, the particles in many cases undergo grain growth during sintering. The resulting composites may therefore have grain sizes that exceed the nano size range by several hundred nanometers even though the starting grain size of the powder mixture is in the nano size range.

Reducing the ceramics to nano sized particles is achieved by conventional particle comminution methods in the nanotechnology industry. A preferred method is high energy ball milling, which can also be used to mix the various powdered components together. This is performed in a high-energy ball mill with the assistance of a large single ball that mixes the particles and applies mechanical impacts to reduce the size of the particles. Enhanced results can be achieved by milling the particles as a suspension in a suspending agent such as a low molecular weight alcohol. The size of the ball, the volume of the ball used per unit volume of powder, the speed of the mill, the temperature at which the milling is performed, and the length of time that milling is continued can all vary widely. Best results will generally be achieved with a milling time ranging from less than an hour to 50 hours or more. The degree of mixing may also be affected by the "charge ratio," which is the ratio of the mass of the ball to the mass of the powder. A charge ratio of from about 5 to about 20 will generally produce the desired results.

Consolidation of the powder mixture into a fused mass that can be used as a medium for conducting electricity and that also has the favorable mechanical characteristics referred to above is accomplished by electric field-assisted sintering, also known as spark plasma sintering. One method of performing this type of sintering is by passing a pulsewise DC electric current through the dry powder mixture or through a consolidated mass of the mixture while applying pressure. A description of spark plasma sintering and apparatus in which this process can be performed is presented by Wang, S. W., et al., "Densification of $Al_2O_3$ powder using spark plasma sintering," *J. Mater. Res.* 15(4), 982–987 (2000). While the conditions may vary, best results will generally be obtained with a densification pressure exceeding 10 MPa, preferably from about 10 MPa to about 200 MPa, and most preferably from about 40 MPa to about 100 MPa. The preferred current is a pulsed DC current of from about 250 $A/cm^2$ to about 10,000 $A/cm^2$, most preferably from about 500 $A/cm^2$ to about 1,500 $A/cm^2$. The duration of the pulsed current will generally range from about 1 minute to about 30 minutes, and preferably from about 1.5 minutes to about 5 minutes. Preferred temperatures are within the range of from about 1,000° C. to about 2,000° C., and most preferably from about 1,400° C. to about 1,700° C. Densification is typically performed by uniaxial compression under vacuum, and preferred vacuum levels for the densification are below 10 Torr, and most preferably below 1 Torr.

The benefits of the invention will be most evident when the composite is densified by spark plasma sintering to a high density, i.e., one that approaches full theoretical density, which is the density of the material as determined by volume averaging the densities of each of its components. A density of at least 95% of the theoretical density is sought, preferably at least 98%, and most preferably at least 99%. The term "relative density" is used herein to denote the actual density expressed as a percent of the theoretical density.

The composites of this invention are useful as conducting media in any application requiring an electrical conduction path in a material that is capable of withstanding extreme conditions of temperature, mechanical stress, or both. The path can assume the form of a coating on an electrically insulating substrate, a lead joining components of an electrical circuit or system of circuits, a wire, a conductive line on printed circuit boards, and any other circuitry application in high performance applications. The range of possibilities will be readily apparent to those skilled in the art.

The following example is offered for purposes of illustration and is not intended to limit the scope of the invention.

EXAMPLE

The polyureasilazane CERASET™ SN, obtained from Commodore Polymer Technologies (Columbus, Ohio, USA), was crosslinked by heating at 200° C. in an argon atmosphere for thirty minutes, then pyrolyzed at 1450° C. in a nitrogen atmosphere for four hours to form an amorphous powder. The powder had an N/C/Si ratio of 42/38/20, on a volumetric basis, and its amorphous character was confirmed by X-ray diffraction analysis. The powder was combined with $TiO_2$ particles of average diameter 32 nm, obtained from Nanophase Technologies Corporation (Burr Ridge, Ill., USA) to form a powder mixture of which the $TiO_2$ constituted 20% by weight. The powder mixture was suspended in ethanol and pulverized for 2 hours by high energy ball milling in a Spex 8000 Mixer/Mill (Spex Certiprep Industries Inc., Metuchen, N.J.) using one tungsten carbide ball 11 mm in diameter and a tungsten carbide vial.

To achieve spark plasma sintering, the powder mixture was placed on a graphite die of inner diameter 20 mm and cold-pressed at 200 MPa. Sintering was performed on a Dr. Sinter 1050 Spark Plasma Sintering System (Sumitomo Coal Mining Company, Japan) under vacuum and an applied pressure of 63 MPa with a pulsed DC current of 5,000 A maximum and a maximum voltage of 10 V. The pulses were 12 ms in duration separated by intervals of 2 ms. The temperature was allowed to reach 1,600° C. and held for three minutes. The temperature was monitored with an optical pyrometer focused on a depression in the graphite die measuring 2 mm in diameter and 5 mm in depth.

The final density of the sintered compact was measured by the Archimedes method using deionized water as the immersion medium. The density was 3.04 $g/cm^3$, which corresponds to 99% theoretical density. Analysis of the sintered compact by X-ray diffraction revealed the presence of three crystalline phases—$\beta$-$Si_3N_4$, SiC, and $TiC_{0.3}N_{0.7}$, combined with transmission electron microscopy, revealed $TiC_{0.3}N_{0.7}$ grains of 100–300 nm incorporated with $Si_3N_4$ and SiC grains of 10–30 nm.

An Agilent 34420A nanoVolt/microOhm meter (Agilent Technologies, Palo Alto, Calif., USA) was used for conductivity measurement using a four-wire probe technique. To remove the effect of extraneous voltages such as those arising due to thermal EMF caused by dissimilar materials in the circuit, two measurements were made: one with the current on and the other with the current off. Using this configuration the meter has a resolution of 0.1 µΩ. The four point probe electrical conductivity (σ) of the sintered composite as measured was $1.74 \times 10^4$ $(\Omega \cdot m)^{-1}$ at room temperature. This value is within the range for electrical conductivity of metals, i.e., above $1 \times 10^4$ $(\Omega \cdot m)^{-1}$.

Hardness and fracture toughness measurements were performed on a Wilson Tukon hardness tester with a diamond Vickers indenter. Bulk specimens were sectioned and mounted in epoxy, then polished through 0.25-micron diamond paste. The indentation parameters for fracture toughness (Kic) were a 2.5 kg load with a dwell time of 15 s. The fracture toughness was calculated by the Anstis equation as disclosed by Anstis, G. R., et al., "A Critical Evaluation of Indentation Techniques for Measuring Fracture Toughness: I, Direct Crack Measurement," *J. Am. Ceram. Soc.* 64(9): 533–538 (1981). The measurements indicated a hardness of 14 GPa and a fracture toughness of 6.7 $MPa \cdot m^{1/2}$.

The foregoing is offered primarily for purposes of illustration and explanation. Further variations, modifications and substitutions that, even though not disclosed herein, still fall within the scope of the invention may readily occur to those skilled in the art.

What is claimed is:

1. An electrically conductive composite of silicon, titanium, carbon, nitrogen, and oxygen, containing $Si_3N_4$ and SiC grains of 10–30 nm, prepared by a process comprising:
   (a) preparing a powder mixture of (i) crystalline titanium dioxide and (ii) a member selected from the group consisting of amorphous silicon carbonitride and a combination of crystalline silicon nitride and silicon carbide, said crystalline titanium dioxide constituting from about 10% to about 40% by weight of said powder mixture; and
   (b) consolidating said powder mixture into a continuous mass by compressing said powder mixture while passing an electric current through said powder mixture, to achieve a fused mass having a density of at least 99% relative to a volume-averaged theoretical density.

2. The electrically conductive composite of claim 1 in which component (ii) of said powder mixture is amorphous silicon carbonitride prepared by pyrolysis of a polyorganosilazane.

3. The electrically conductive composite of claim 1 in which component (ii) of said powder mixture is amorphous silicon carbonitride prepared by pyrolysis of a polyureasilazane.

4. The electrically conductive composite of claim 1 in which said crystalline titanium dioxide consists of particles averaging less than 100 nm in diameter.

5. The electrically conductive composite of claim 1 in which said crystalline titanium dioxide consists of particles averaging less than 50 nm in diameter.

6. The electrically conductive composite of claim 1 in which step (b) comprises compressing said powder mixture at a pressure of about 10 MPa to about 200 MPa and a temperature of from about 1,000° C. to about 2,000° C., and said electric current is a pulsed direct current of about 250 $A/cm^2$ to about 10,000 $A/cm^2$.

7. The electrically conductive composite of claim 6 in which said pressure is from about 40 MPa to about 100 MPa.

8. The electrically conductive composite of claim 6 in which said temperature is from about 1,400° C. to about 1,700° C.

9. The electrically conductive composite of claim 6 in which said pulsed electric current is from about 500 $A/cm^2$ to about 1,500 $A/cm^2$.

10. The electrically conductive composite of claim 6 in which said pressure is from about 40 MPa to about 100 MPa, said temperature is from about 1,400° C. to about 1,700° C., and said pulsed electric current is from about 500 $A/cm^2$ to about 1,500 $A/cm^2$.

11. In an application requiring the conduction of an electric current as the result of a voltage applied between two terminals, the improvement comprising interposing an electrically conductive composite of silicon, titanium, carbon and nitrogen containing $Si_3N_4$ and SiC grains of 10–30 nm, between said terminals to provide an effective electrical conduction path, said composite formed by consolidating a powder mixture consisting essentially of (i) crystalline titanium dioxide and (ii) a member selected from the group consisting of amorphous silicon carbonitride and a combination of crystalline silicon nitride and silicon carbide, said crystalline titanium dioxide constituting from about 10% to about 40% by weight of said powder mixture, into a fused mass by compressing said powder mixture while passing an electric current through said powder mixture, said composite having a density of at least 95% relative to volume averaged theoretical density.

12. The improvement of claim 11 in which said density is at least 98% relative to said volume-averaged theoretical density.

13. The improvement of claim 11 in which said density is at least 99% relative to said volume-averaged theoretical density.

14. The improvement of claim 11 in which component (ii) of said powder mixture is amorphous silicon carbonitride prepared by pyrolysis of a polyorganosilazane.

15. The improvement of claim 11 in which component (ii) of said powder mixture is amorphous silicon carbonitride prepared by pyrolysis of a polyureasilazane.

16. The improvement of claim 11 in which said crystalline titanium dioxide consists of particles averaging less than 100 nm in diameter.

17. The improvement of claim 11 in which said crystalline titanium dioxide consists of particles averaging less than 50 nm in diameter.

18. The improvement of claim 11 in which step (b) comprises compressing said powder mixture at a pressure of from about 10 MPa to about 200 MPa and a temperature of from about 1,000° C. to about 2,000° C., and said electric current is a pulsed direct current of about 250 $A/cm^2$ to about 10,000 $A/cm^2$.

19. The improvement of claim 18 in which said pressure is from about 40 MPa to about 100 MPa.

20. The improvement of claim 18 in which said temperature is from about 1,400° C. to about 1,700° C.

21. The improvement of claim 18 in which said pulsed electric current is from about 500 $A/cm^2$ to about 1,500 $A/cm^2$.

22. The improvement of claim 18 in which said pressure is from about 40 MPa to about 100 MPa, said temperature is from about 1,400° C. to about 1,700° C., and said pulsed electric current is from about 500 $A/cm^2$ to about 1,500 $A/cm^2$.

* * * * *